(12) United States Patent
Taekema et al.

(10) Patent No.: US 10,845,766 B2
(45) Date of Patent: Nov. 24, 2020

(54) WAKE-UP LIGHT WITH ADJUSTABLE LCD DISPLAY

(71) Applicant: KONINKLIJKE PHILIPS N.V., Eindhoven (NL)

(72) Inventors: Harko Jan Taekema, Drachten (NL); Michiel Hans Zeinstra, Blauwhuis (NL); Jeroen Beutick, Zwolle (NL); Michiel Heersema, Groningen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/632,563

(22) PCT Filed: Jul. 19, 2018

(86) PCT No.: PCT/EP2018/069602
§ 371 (c)(1),
(2) Date: Jan. 21, 2020

(87) PCT Pub. No.: WO2019/020479
PCT Pub. Date: Jan. 31, 2019

(65) Prior Publication Data
US 2020/0160798 A1 May 21, 2020

(30) Foreign Application Priority Data

Jul. 25, 2017 (EP) ..................................... 17182920

(51) Int. Cl.
*G04G 11/00* (2006.01)
*G04G 9/00* (2006.01)
(Continued)

(52) U.S. Cl.
CPC ........... *G04G 11/00* (2013.01); *G04G 9/0094* (2013.01); *G04G 15/00* (2013.01); *G04G 15/006* (2013.01);
(Continued)

(58) Field of Classification Search
CPC ................................................... G04G 9/0094
See application file for complete search history.

(56) References Cited

U.S. PATENT DOCUMENTS

2010/0232261 A1* 9/2010 Suen ....................... G04G 11/00
368/256
2010/0244740 A1 9/2010 Alpert et al.
(Continued)

FOREIGN PATENT DOCUMENTS

| DE | 2555859 A1 | 6/1976 |
| GB | 729776 A | 5/1955 |
| GB | 226166 A | 6/2009 |
| WO | 2009077941 A1 | 6/2006 |
| WO | 2009101557 A1 | 8/2009 |
| WO | 2010/015990 A2 | 2/2010 |

(Continued)

OTHER PUBLICATIONS

Zhang, Philips HF3520 Wake-Up LED Light Review, Overview, Functions, Demonstration, Screen Capture of YouTube Video Clip published Nov. 9, 2015 (Year: 2015).*
(Continued)

*Primary Examiner* — Evan P Dzierzynski
*Assistant Examiner* — Keith G. Delahoussaye

(57) ABSTRACT

According to an aspect, there is provided a light apparatus, the light apparatus comprising an outer housing comprising a translucent portion; a main light source positioned inside the outer housing for generating light, wherein light generated by the main light source is incident on the translucent portion; and a display light source positioned inside the outer housing for projecting information onto a part of the translucent portion on which light is incident from the main light source.

20 Claims, 2 Drawing Sheets

(51) Int. Cl.
- *G04G 15/00* (2006.01)
- *G09G 3/34* (2006.01)
- *F21Y 113/20* (2016.01)
- *F21Y 113/17* (2016.01)
- *F21V 33/00* (2006.01)
- *G04B 45/00* (2006.01)
- *G09G 3/32* (2016.01)
- *G09G 3/36* (2006.01)

(52) U.S. Cl.
CPC ........ *G09G 3/3406* (2013.01); *F21V 33/0056* (2013.01); *F21Y 2113/17* (2016.08); *F21Y 2113/20* (2016.08); *G04B 45/00* (2013.01); *G09G 3/32* (2013.01); *G09G 3/36* (2013.01); *G09G 2320/0626* (2013.01)

(56) References Cited

U.S. PATENT DOCUMENTS

2015/0276178 A1* 10/2015 Chien ................. F21V 23/0442
　　　　　　　　　　　　　　　　　　　　　　362/95
2017/0321850 A1* 11/2017 Chien ...................... F21K 9/60

FOREIGN PATENT DOCUMENTS

| WO | 2010092511 A1 | 8/2010 |
| WO | 2013156927 A1 | 10/2013 |

OTHER PUBLICATIONS

International Search Report and Written Opinion, International Application No. PCT/EP2018/069602, dated Oct. 18, 2018.

\* cited by examiner

WAKE-UP LIGHT WITH ADJUSTABLE LCD DISPLAY

CROSS-REFERENCE TO PRIOR APPLICATIONS

This application is the U.S. National Phase application under 35 U.S.C. § 371 of International Application Serial No. PCT/EP2018/069602, filed on 19 Jul. 2018, which claims the benefit of European 17182920.3, filed on 25 Jul. 2017. These applications are hereby incorporated by reference herein.

TECHNICAL FIELD OF THE INVENTION

The invention relates to an improved light apparatus that can be used as a wake-up light or a light apparatus for providing light therapy.

BACKGROUND TO THE INVENTION

As an alternative to a standard alarm clock, or a phone as an alarm, a so-called wake-up light can be placed on a night stand or bedside table. A wake-up light can be used to gradually increase the intensity of the light produced to help wake a user from sleep more naturally. In some cases, the colour of the light produced by the wake-up light can be adjusted to mimic the colours produced during a sunrise. In addition to providing this lighting or wake-up function, a wake-up light typically also includes a display for displaying information to a user, such as the time, an alarm time, settings for the wake-up light, etc. This information may be visible when the wake-up light is switched off, and when the wake-up light is producing light. The Philips Wake-Up Light HF3520 is an example of this type of wake-up light.

It is desirable for these wake-up lights to be as small as possible, for example in view of the limited space available by a bed. However, reducing the size of the light emitting part of a housing means that the brightness of the light source and/or the brightness of the light emitting part of the housing needs to be increased in order to maintain a given amount of light output. This may decrease the comfort for the user of the light, since the wake-up light may be uncomfortably bright to look at.

SUMMARY OF THE INVENTION

It has been recognised that one of the constraints on reducing the size of a wake-up light is the presence of the display on the front of the wake-up light (the front of the wake-up light being the side that is typically oriented towards the user). As shown in FIG. 1, which is a representation of the front of the Philips HF3520 Wake-Up Light, the wake-up light 2 comprises a housing 3 having an illuminating portion 4 that is for illumination by a light source and a display portion 6 on which information 8, such as the time, is displayed. The illuminating portion 4 and display portion 6 are both translucent portions of the housing 3 (and indeed in the Philips HF3520 the entire front face is a single translucent shell). However, the display portion 6 of the housing 3 is not illuminated by the light source that illuminates the illuminating portion 4 and so the presence of the display portion 6 either increases the overall size of the wake-up light or requires a brighter light to produce the same level of light output as a larger illuminating portion 4 (in which case the brightness of the display portion 6 may also need to be increased to ensure that it is still visible when the wake-up light is on).

Thus, when designing such a wake-up light, there is a trade-off between the optimum display brightness (where lower is better), the optimum light output by the wake-up light (i.e. to meet a minimum threshold) and the size of the wake-up light (where smaller is better). The same requirements apply for any type of light therapy device having a display, particularly those that are intended to be portable. Likewise, these requirements can apply to so-called mood lighting that provide coloured light to suit a user•s mood.

Therefore there is a need for an improved light apparatus that is able to display information.

According to an aspect, there is provided a light apparatus, the light apparatus comprising an outer housing comprising a translucent portion; a main light source positioned inside the outer housing for generating light, wherein light generated by the main light source is incident on the translucent portion; and a display light source for projecting information onto a part of the translucent portion on which light is incident from the main light source.

These and other aspects of the invention will be apparent from and elucidated with reference to the embodiment(s) described hereinafter.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

As noted above, it is desirable to reduce the size of a light apparatus, such as that used as a wake-up light, but this should not be at the expense of having to increase the brightness of the light source in order to maintain the same level of illumination in the environment.

Figure 1:
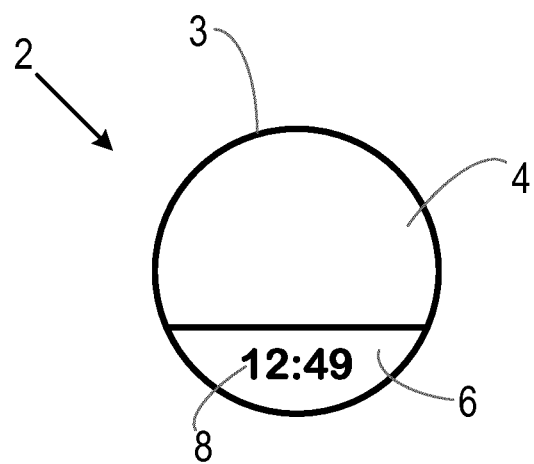
FIG. 1 is a representation of the front of a Philips HF3520 Wake-Up Light.

It has been recognised that one of the constraints on reducing the size of a wake-up light is the presence of the display on the front of the wake-up light, as shown in FIG. 1. In the Philips HF3520 Wake-Up Light, although the front of the device is a single •shell• of translucent material, the display portion 6 is separated from the illumination portion 4 so that the light source that illuminates the illumination portion 4 does not illuminate the display portion 6, and so the display portion 6 does not contribute to the lighting functionality of the wake-up light. Typically in a wake-up light only around 60-80% of the front surface can be used for lighting, with the remaining part of the front surface (20-40%) being used for the display portion 6 and/or any user interface components (e.g. switches, buttons, etc.).

Thus, in conventional light apparatus, the components providing the information 8 for display on the display portion 6 may be in a separate part of the housing to the light source for the illuminating portion 4 (so the area inside the apparatus behind the display portion 6 is optically separated from the light source for the illuminating portion). Alternatively, the components for providing the information 8 for display on the display portion may be directly attached to the front shell 3 to display the information 8 at that location, but since such components are not transparent, they block the light from the light source and thereby reduce the light output by the apparatus.

In view of these problems, the invention provides a light apparatus that comprises an outer housing having a translucent portion (for example a front shell of the apparatus), a main light source positioned inside the outer housing for generating light, with the light from the main light source being incident on the translucent portion, and a display light source positioned inside the outer housing that projects information onto the translucent portion, and specifically onto a part of the translucent portion on which light is incident from the main light source. In this way, the information, such as the time, an alarm time, apparatus settings, etc. is overlaid on parts of the translucent portion that are lit by the main light source. This avoids the need for a separate, un-illuminated, display portion on the apparatus, resulting in a more compact apparatus.

Figure 2:
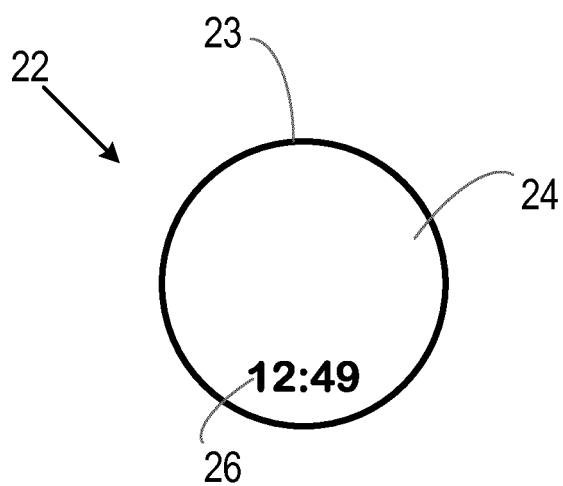
FIG. 2 is a representation of the front of an exemplary light apparatus according to a first embodiment when in use.

FIG. 2 shows a front view of an exemplary light apparatus according to a first embodiment. The light apparatus 22 comprises a housing 23 or shell having a translucent portion 24 (the entire front surface in this example), and information 26 is projected onto the translucent portion 24 by display components inside the housing 23 so that it is visible to a user looking at the light apparatus 22. The information 26 can be the time, an alarm time, settings for the wake-up light, etc., and as such the information 26 can comprise one or more letters, words, numbers and symbols (which includes graphical icons). Therefore the information 26 projected onto the translucent portion 24 can comprise one or more alphanumeric characters (i.e. letters and/or numerals) and/or symbols. For example one or more alphanumeric characters and/or symbols can be projected onto the translucent portion 24 to display the time or an alarm time to the user. It will be appreciated that the circular shape of the front surface of the light apparatus 22 is merely exemplary, and other shapes or configurations can be used. Likewise, although this example shows the translucent portion 24 as the whole of the front surface, it will be appreciated that other designs are possible, for example the translucent portion 24 could have a border.

Figure 3:
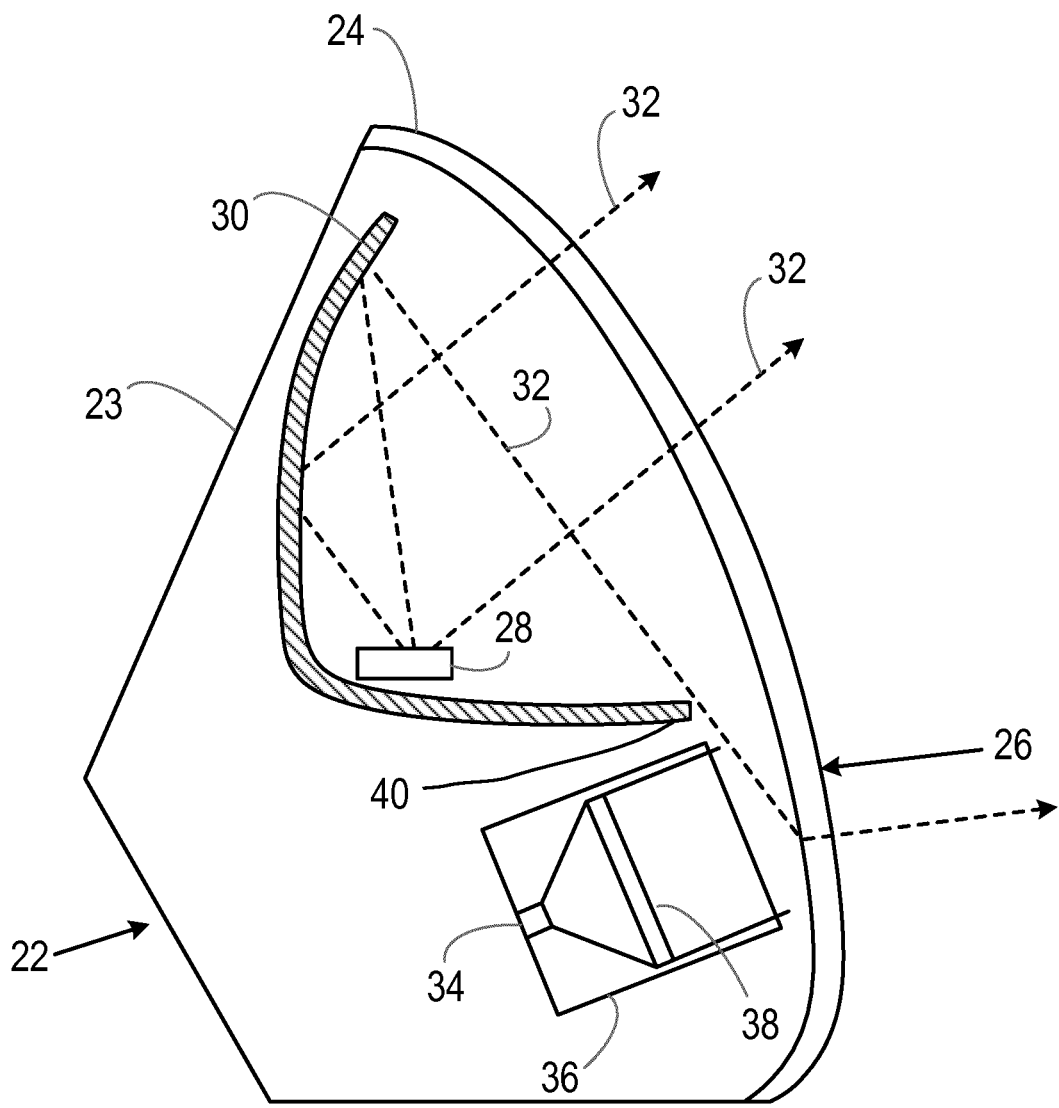
FIG. 3 is a schematic diagram of a cross-section through a light apparatus according to the first embodiment.

FIG. 3 is a schematic diagram of a cross-section through the light apparatus 22 according to the first embodiment. The light apparatus 22 comprises an outer housing 23, within which all of the components of the light apparatus 22 are contained. At least a part of the outer housing 23 is translucent, which forms a translucent portion 24. Thus, at least a part of the outer housing 23 is formed from a translucent material. The translucent portion of the housing 23 can be formed from a plastic, such as polycarbonate, which can include a filler or colouring compound, or a more transparent material, such as polymethyl methacrylate (PMMA) or glass. The filler preferably has high reflective properties to minimise losses due to light being absorbed in the translucent portion. One example of a filler is titanium dioxide, although those skilled in the art will be aware of other types of filler that can be used. In the example of FIG. 3, the entire •front• face of the light apparatus 22 (i.e. the side of the light apparatus 22 that is typically oriented towards a user) is the translucent portion 24, but this should not be considered to be limiting. For example in other embodiments part of a front face could form the translucent portion 24, or the entire outer housing 23 (so including the sides and back of the apparatus 22) could be the translucent portion 24.

The light apparatus 22 comprises a main light source 28 that is positioned or arranged inside the outer housing 23 so that the light generated by the main light source 28 is able to illuminate the translucent portion 24 of the outer housing 23, and thus illuminate the environment around the light apparatus 22. The main light source 28 can be a light emitting diode (LED) based light source that includes one or more LEDs. The one or more LEDs can comprise LEDs having one or more colours that are controllable individually and/or in combination to produce light of a desired colour and/or light of a desired brightness or luminance. As an alternative to LEDs, the main light source 28 could be one or more organic LEDs (OLEDs), halogen bulbs, incandescent bulbs or low-pressure mercury bulbs. In another alternative, the translucent portion 24 can be configured as a remote phosphor for the main light source 28 (e.g. an LED), with the main light source 28 generating blue light and the remote phosphor in the translucent portion 24 transferring the blue light to white. Thus, the main light source 28 can be configured to provide light at varying brightness or luminance levels and/or with varying colours. In embodiments where the light apparatus 22 is a wake-up light, the main light source 28 can be controllable to gradually increase the light output and to change the colour of the light to mimic a sunrise. In embodiments where the light apparatus 22 is to provide so-called •mood• lighting, the main light source 28 can be controllable to gradually change the light output and to change the colour of the light to suit a desired mood.

Some light from the main light source 28 may be directly incident on the translucent portion 24 and/or some light from the main light source 28 may be directed to the translucent portion 24 via one or more reflectors 30. Various light rays 32 are shown in FIG. 3 illustrating how light from the main light source 28 can be incident on the various parts of the translucent portion 24.

With a suitably shaped reflector 30 or arrangement of reflectors 30, the light 32 from the main light source 28 can be distributed relatively evenly over the translucent portion 24, which can be desirable for a wake-up light, or other light apparatus 22 where it is desirable to provide an even illumination of the translucent portion 24. In some embodiments, a surface texture could be applied to the surface of the reflectors 30 to lead to the diffusing of the reflected light.

In addition, or as an alternative, an even (or more even) distribution of light can be achieved by the translucent portion 24 being configured or formed so that it diffuses light that is incident from the main light source 28. The translucent portion 24 can be formed from a material that has diffusing properties due to texture or structure, such as frosted glass. Surface texture can be applied through use of a mould or as a surface treatment like sand blasting. Alternatively, transparent beads, such as glass spheres, can be added throughout the material to refract the light. As indicated above, any colouring agent in the material will also help to diffuse light. Generally an optimum solution is sought that has high refractive and reflective properties and low absorbing properties. Titanium dioxide has been found to be a suitable commercially viable solution for forming a translucent portion 24. Having the translucent portion 24 formed from a diffusing material or having diffusing properties provides the advantage that of the all internal components of the light apparatus 22 can be masked, like the display components and the reflectors 30, from a user of the apparatus 22. As an alternative to the outer housing 23/translucent portion 24 being the diffuser, a diffuser or diffusing material can be located against the outer housing (e.g. as a separate layer or component of material).

As a further option or as an alternative, the light apparatus 22 can comprise one or more diffusers inside the outer housing 23 that are configured or arranged to diffuse the light generated by the main light source 28, so that the light is already diffuse when it is incident on the translucent portion 24. Typically a diffuser is placed near to the main light source 28 (particularly where the main light source 28 is formed from a number of light sources, such as LEDs), as this helps to directly •bundle• the light from these lights sources into a single more uniform light source before the light reaches the reflector(s) 30. If this is not possible (for example due to the design constraints on the light apparatus 22), then a diffuser can be placed directly after the reflector 30 (so that light reflected from the reflector 30 is then incident on the diffuser).

The above arrangements provide that the light from the main light source 28 is •mixed• so it illuminates much of the translucent portion 24, resulting in the translucent portion 24 acting as a diffuse light emitting panel.

A display light source 34 is also shown in FIG. 3. The display light source 34 is positioned inside the outer housing 23 to provide the light for projecting the information 26 on the translucent portion 24. As noted above, the information 26 projected on the translucent portion 24 can comprise one or more alphanumeric characters (i.e. letters and/or numerals) and/or symbols. For example one or more alphanumeric characters and/or symbols can be projected onto the translucent portion 24 to display the time or an alarm time to the user. Since the portion 24 is translucent, the information 26 will be visible on the outside of the outer housing 23, and so the one or more alphanumeric characters and/or symbols are visible on the outside of the outer housing 23. The display light source 34 can be a light emitting diode (LED) based light source that includes one or more LEDs. The one or more LEDs can comprise LEDs having one or more colours that are controllable individually and/or in combination to produce light of a desired colour and/or light of a desired brightness. As an alternative to LEDs, the display light source 34 could be one or more organic LEDs (OLEDs), halogen bulbs, incandescent bulbs or low-pressure mercury bulbs. In another alternative, where the translucent portion 24 is configured as a remote phosphor for the main light source 28, the display light source 34 can generate a different tint or shade of blue light and the remote phosphor in the translucent portion 24 will transfer this different tint or shade of blue light to a different white colour (i.e. different to the white colour produced by the blue light from the main light source 28). In any case, the display light source 34 should provide a small light emitting surface to improve the sharpness of the resulting information display and reduce image ghosting.

In some embodiments, the display light source 34 can be configured to project the information on the part of the translucent portion using collimated light (i.e. parallel light), so that the information 26 is visible on the translucent portion 24 in addition to the translucent portion 24 being illuminated by the light from the main light source 28. In alternative embodiments, the display light source 34 can act as a point source that emits light rays in a conical direction to produce a slightly magnified but clear image of the information 26 on the translucent portion 24.

In some embodiments, the display light source 34 can be configured or controllable to generate light having a different colour to the light 32 generated by the main light source 28. The use of different, e.g. contrasting, colours means that the information 26 will be more easily readable by a user of the light apparatus 22. In some embodiments, particularly where the colour of the light generated by the main light source 28 is changed during operation of the apparatus 22 to mimic a sunrise (or for any other reason, e.g. in the case of mood lighting), the colour of the light generated by the display light source 34 can be adjusted or changed in order to maintain visibility of the information 26. For example the display light source 34 could project the information 26 onto the translucent portion 24 using red light when the main light source 28 is generating white light, but the display light source 34 can switch to projecting the information 26 onto the translucent portion 24 using, e.g. yellow light if the main light source 28 is generating red light, for example to mimic a sunrise.

In some embodiments, the display light source 34 can be configured or controllable to generate light having a higher luminance or brightness at the translucent portion 24 to the light 32 generated by the main light source 28 at the translucent portion 24. In this way, the information 26 will be projected on the translucent portion 24 at a higher brightness or luminance level than the brightness or luminance of the translucent portion 24 caused by the light from the main light source 28, which means that the information 26 is more easily visible to a user. In some embodiments, particularly where the brightness or luminance of the light generated by the main light source 28 is changed during operation of the apparatus 22 to mimic a sunrise (or for any other reason, e.g. in the case of mood lighting), the brightness or luminance of the light generated by the display light source 34 can be adjusted or changed in order to maintain visibility of the information 26. In these embodiments (or indeed generally), the light apparatus 22 can include a light sensor to measure one or both of the light level/intensity outside the apparatus 22 and the light level/intensity emitted by the apparatus 22. The signal from the light sensor can be used to adjust the brightness or luminance of the light generated by the display light source 34. In some embodiments, the light sensor can be located inside the outer housing 23 and close to the display light source 34 or the part of the translucent portion 24 on which the information is projected. This location for the light sensor provides the benefit that the brightness/intensity of the light entering the apparatus 22 from the environment can be measured along with the brightness/intensity of the light from the main light source 28.

In some embodiments, the light generated by the display light source 34 can have a different colour and a different (higher) brightness or luminance than the light generated by the main light source 28.

In the example of FIG. 3 the display light source 34 is part of a display module 36 that also comprises a transmissive display panel, such as a liquid crystal display, LCD, panel 38. As an alternative to an LCD panel, a digital light processing (DLP) chip could be used to generate the information to display. In the following explanation of FIG. 3 reference is made to an LCD panel, but it will be appreciated that another type of transmissive display panel or a DLP chip could be used instead. In this embodiment, the display light source 26 generates light and illuminates the LCD panel 38, and segments or pixels in the LCD panel 38 selectively block and transmit light as required to project the required information 26 onto the translucent portion 24 (i.e. segments or pixels in the LCD panel 38 selectively block and transmit light as required to project the alphanumeric characters and/or symbols forming the information 26 on the translucent portion 24). Thus the LCD panel 38 can be a transmissive LCD panel.

To further improve the amount of light reaching the translucent portion 24 in front of the display light source 34 where the information 26 is displayed, since the display side of an LCD panel 38 can typically be black or dark, a one-way mirror foil can be arranged on the LCD panel 38 (for example one of the polarisers of the LCD panel 38 can comprise the one-way mirror foil) so that light generated by the main light source 28 that is incident on the LCD panel 38 is reflected by the one-way mirror foil towards the translucent portion 24.

In the example embodiment shown in FIG. 3, the display module 36/display light source 34 is positioned in a lower portion of the outer housing 23, with the main light source 28 positioned in an upper portion. The display module 36 should be spaced from the translucent portion 24 to enable light from the main light source 28 to be incident on the part of the translucent portion 24 on which the display light source 34 projects the information 26. The reflector(s) 30 provided in the upper portion are configured so that some of the light 32 generated by the main light source 28 is reflected towards the lower portion, and in particular towards the part of the translucent portion 24 in front of the display module 36/display light source 34. Thus, the reflector(s) 30 are configured so that there is a gap between the end 40 of the reflector 30 and the translucent portion 24. This gap may be an air gap or may be filled by a transparent material. This arrangement is in contrast to conventional wake-up lights in which the display module 36/display light source 34 is optically separated from the main light source 28.

In some embodiments, to increase the amount of light from the main light source 28 reaching the lower portion of the apparatus 22, part of the inner surface of the translucent portion 24 can be configured to be partially reflecting such that some of the light generated by the main light 28 that is incident on the translucent portion 24 is reflected towards another part of the apparatus 22, particularly the part where the information 26 is displayed. For example, in the embodiment shown in FIG. 3, a part of the translucent portion 24 near the top of the apparatus 22 could be partially reflecting so that some of the light 32 from the main light source 28 is reflected towards the lower part of the apparatus 22. In a variation to this embodiment, the entire translucent portion 24 could be partially reflecting. In either case, a filler such as titanium dioxide could be used to provide this property.

Although not shown in FIG. 3, the light apparatus 22 can include additional components to those shown. For example the light apparatus 22 can include a power source, for example a battery, or a means for connecting to a mains power supply, for powering the light apparatus 22. The light apparatus 22 can also include a speaker for producing sound, such as alarm sounds, voice messages or music. The light apparatus 22 can also include a control unit that can control the operations of the light apparatus 22, such as controlling or determining the information 26 to be displayed by the display light source 34, and controlling the brightness and/or colour of the light generated by the main light source 28 and/or the light generated by the display light source 34.

Another additional component or components can include one or more user interface components that enable a user to control or operate the apparatus 22. For example the user interface components can include one or more buttons, switches, keys, etc. or one or more touch panels/buttons. The user interface components can be located in any desired position on the apparatus 22, but advantageously a touch panel(s) or touch button(s) can be provided on the translucent portion 24 to minimise any extra size of the apparatus 22 required to implement a user interface. In some implementations, a touch panel or touch button can be overlaid on the part of the translucent portion 24 on which the information 26 is displayed to create a touch screen. In other implementations, the circuitry required to implement a touch panel or touch button (e.g. a transparent foil) can be placed in any desired location on the translucent portion 24 (for example with a graphic or image printed onto the translucent portion 24 to indicate the user interface). The touch panel or touch button can use any of capacitive, resistive, inductive or optical sensing technologies to sense touches by the user.

It will be appreciated that the specific arrangement or configuration of the main light source 28, display light source 34, reflector(s) 30 and diffuser(s) will depend on their relative positions in the light apparatus 22 and the shape of the outer housing 23 (and the shape of the translucent portion 24).

For example, in some alternative arrangements, the information can be displayed in a central portion or an upper portion of the front face of an apparatus. In another alternative arrangement, rather than provide the display light source 34 in a separate part of the outer housing 23, the display light source 34 could be located much closer to the main light source 28, for example they could be adjacent, or otherwise both located within a reflector 30. In this case, the reflector(s) 30 should be arranged or configured so that the light from the main light source 28 is sufficiently reflected and mixed up so that the presence of the display light source 34 (and any associated components, such as an LCD panel 38) are not visible to a user of the light apparatus 22. In a further alternative arrangement, with a suitable arrangement of reflector(s) 30, the display light source 34 and/or the main light source 28 could be located out of line of sight of the translucent portion 24. For example the display light source 34 could be positioned at the rear of the apparatus 22 and a reflector 30 could be positioned to direct the information light 26 to the translucent portion 24.

Although in the embodiments described above the display light source 34 is positioned inside the outer housing 23/translucent portion 24, it will be appreciated that in alternative embodiments the display light source 34/display module 36 could instead be located outside the outer housing 23 and the display light source 34/display module 36 could project the information to be displayed onto the outside of the translucent portion 24. This would produce the same visual result as the embodiments described above, i.e. the information projected on to part of the translucent portion that is illuminated by light from the main light source 28.

Therefore there is provided an improved light apparatus 22 that is able to display information. In particular, by projecting the information 26 onto part of the translucent portion 24 that is also illuminated by the main light source 28, the efficiency of the light apparatus 22 is improved in terms of the space taken up by the apparatus 22 relative to the brightness of the light that is to be generated.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light apparatus, the light apparatus comprising:
an outer housing comprising a translucent portion;
a main light source positioned inside the outer housing configured to generate light, wherein light generated by the main light source is incident on the translucent portion;
a display light source configured to project information that comprises one or more alphanumeric characters and/or symbols onto a part of the translucent portion on which light is incident from the main light source; and
one or more reflectors inside the outer housing that are configured to reflect some of the light generated by the main light source toward the part of the translucent housing on which the display light source projects the information.

2. The light apparatus as claimed in claim 1, wherein the display light source is a light emitting diode (LED) based light source.

3. The light apparatus as claimed in claim 1, wherein the display light source is configured to generate collimated light to project the information on the part of the translucent portion.

4. The light apparatus as claimed in claim 1, wherein the display light source is configured to generate light having a different color than the light generated by the main light source.

5. The light apparatus as claimed in claim 1, wherein the display light source is configured to generate light having a higher luminance or brightness than the light generated by the main light source.

6. The light apparatus as claimed in claim 1, wherein the display light source is configured to generate light having a higher luminance or brightness at the translucent portion than the light generated by the main light source.

7. The light apparatus as claimed in claim 1, wherein the translucent portion is configured to diffuse the light generated by the main light source that is incident thereon.

8. The light apparatus as claimed in claim 1, wherein the light generated by the main light source is diffuse when it is incident onto the translucent portion.

9. The light apparatus as claimed in claim 1, wherein a part of the inner surface of the translucent portion is configured to be partially reflecting such that some of the light generated by the main light and incident thereon is reflected.

10. The light apparatus as claimed in claim 1, wherein the display light source is part of a display module that is spaced from the translucent portion to enable light from the main light source to be incident on the part of the translucent portion on which the display light source projects the information.

11. The light apparatus as claimed in claim 10, wherein the display module further comprises a liquid crystal display (LCD) panel, and herein the information is projected by the display light source to illuminate segments or pixels of the LCD panel.

12. The light apparatus as claimed in claim 11, wherein the LCD panel comprises a one-way mirror foil arranged such that light generated by the main light source that is incident on the LCD panel is reflected by the one-way mirror foil.

13. The light apparatus as claimed in claim 1, wherein the display light source is positioned inside the outer housing.

14. The light apparatus as claimed in claim 1, further comprising:
a light sensor positioned near to the display light source or the part of the translucent portion on which the information is projected, wherein the light sensor is for measuring the level or intensity of light from the environment and the main light source.

15. A method comprising:
generating light, with a main light source positioned inside an outer housing comprising a translucent portion, wherein light generated by the main light source is incident on the translucent portion;
projecting, with a display light source, information that comprises one or more alphanumeric characters and/or symbols onto a part of the translucent portion on which light is incident from the main light source; and
reflecting, with one or more reflectors inside the outer housing, some of the light generated by the main light source toward the part of the translucent housing on which the display light source projects the information.

16. The method of claim 15, further comprising:
generating, with the display light source, collimated light to project the information on the part of the translucent portion.

17. The method of claim 15 further comprising:
generating, with the display light source, light having a different color than the light generated by the main light source.

18. The method of claim 15, further comprising:
generating, with the display light source, light having a higher luminance or brightness than the light generated by the main light source.

19. The method of claim 15, further comprising:
diffusing, with the translucent portion, the light generated by the main light source that is incident thereon.

20. An apparatus comprising:
means for generating light, with a main light source positioned inside an outer housing comprising a translucent portion, wherein light generated by the main light source is incident on the translucent portion;
means for projecting, with a display light source, information that comprises one or more alphanumeric characters and/or symbols onto a part of the translucent portion on which light is incident from the main light source; and
means for reflecting, with one or more reflectors inside the outer housing, some of the light generated by the main light source toward the part of the translucent housing on which the display light source projects the information.

* * * * *